(12) United States Patent
Wieters et al.

(10) Patent No.: US 9,474,437 B2
(45) Date of Patent: Oct. 25, 2016

(54) ENDOSCOPE HAVING A SHAFT TUBE

(75) Inventors: Martin Wieters, Hamburg (DE); Philipp Abel, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 13/885,797

(22) PCT Filed: Oct. 20, 2011

(86) PCT No.: PCT/EP2011/005284
§ 371 (c)(1),
(2), (4) Date: Jun. 11, 2013

(87) PCT Pub. No.: WO2012/089289
PCT Pub. Date: Jul. 5, 2012

(65) Prior Publication Data
US 2013/0267782 A1    Oct. 10, 2013

(30) Foreign Application Priority Data

Dec. 27, 2010   (DE) .................. 10 2010 056 025

(51) Int. Cl.
| | | |
|---|---|---|
| *A61B 1/06* | (2006.01) | |
| *A61B 1/00* | (2006.01) | |
| *G02B 23/24* | (2006.01) | |
| *G02B 23/26* | (2006.01) | |

(52) U.S. Cl.
CPC ....... *A61B 1/00167* (2013.01); *G02B 23/2469* (2013.01); *G02B 23/26* (2013.01)

(58) Field of Classification Search
CPC ............ A61B 1/0008; A61B 1/00096; A61B 1/00167; A61B 1/00174; A61B 1/00177; A61B 1/00179; A61B 1/00181

USPC ....... 600/121, 123, 128, 130, 166, 171, 182; 604/21; 348/45, 65

See application file for complete search history.

(56) References Cited

U.S. PATENT DOCUMENTS

| | | | |
|---|---|---|---|
| 4,706,656 A | 11/1987 | Kuboto | |
| 4,802,460 A | 2/1989 | Ohkuwa et al. | |
| 4,838,247 A * | 6/1989 | Forkner | ........................ 600/173 |
| 4,867,138 A | 9/1989 | Kubota et al. | |
| 5,423,312 A | 6/1995 | Siegmund et al. | |

(Continued)

FOREIGN PATENT DOCUMENTS

| | | |
|---|---|---|
| DE | 296 20 824 U1 | 4/1997 |
| DE | 197 20 163 A1 | 11/1997 |

(Continued)

OTHER PUBLICATIONS

Sodji et al. (DE 198 40 862), machine translation on Jan. 22, 2015 from espacenet.com, 11 pages.*

(Continued)

*Primary Examiner* — Anhtuan T Nguyen
*Assistant Examiner* — Timothy J Neal
(74) *Attorney, Agent, or Firm* — Scully, Scott, Murphy & Presser, PC

(57) ABSTRACT

An endoscope including: a shaft tube; a fibre tube disposed within the shaft tube; an image guide having a distal objective, the image guide being disposed within the shaft tube; and an optical fibre bundle disposed in a free cross-section between the fibre tube and the shaft tube. Wherein the fibre tube has an elongate cross-section.

5 Claims, 1 Drawing Sheet

(56) References Cited

U.S. PATENT DOCUMENTS

| | | | |
|---|---|---|---|
| 5,630,784 A | 5/1997 | Siegmund et al. | |
| 6,324,742 B1 | 12/2001 | Odanaka | |
| 6,471,639 B2 * | 10/2002 | Rudischhauser | A61B 1/00135 600/128 |
| 6,827,710 B1 * | 12/2004 | Mooney et al. | 604/500 |
| 6,840,909 B2 * | 1/2005 | Gatto | 600/562 |
| 7,108,657 B2 * | 9/2006 | Irion et al. | 600/110 |
| 2001/0056222 A1 | 12/2001 | Rudischhauser et al. | |
| 2005/0085692 A1 | 4/2005 | Kiehn et al. | |
| 2005/0203341 A1 * | 9/2005 | Welker et al. | 600/130 |
| 2005/0250992 A1 | 11/2005 | Scherr | |
| 2006/0036132 A1 | 2/2006 | Renner et al. | |

FOREIGN PATENT DOCUMENTS

| | | | |
|---|---|---|---|
| DE | 198 40 862 A1 | 3/2000 | |
| DE | 19840862 A1 * | 3/2000 | G02B 23/24 |
| DE | 201 21 717 U1 | 3/2003 | |
| DE | 103 07 903 A1 | 9/2004 | |
| DE | 10 2004 023 024 A1 | 12/2005 | |
| DE | 10 2007 002 042 A1 | 7/2008 | |
| EP | 1 523 932 A1 | 4/2005 | |
| JP | 2010-075321 A | 4/2010 | |

OTHER PUBLICATIONS

International Search Report dated Jan. 2, 2012 issued in PCT/EP2011/005284.

English Abstract of JP 9304693 A dated Nov. 28, 1997.

English translation of International Preliminary Report on Patentability together with the Written Opinion dated Jul. 11, 2013 received in related International Application No. PCT/EP2011/005284.

* cited by examiner

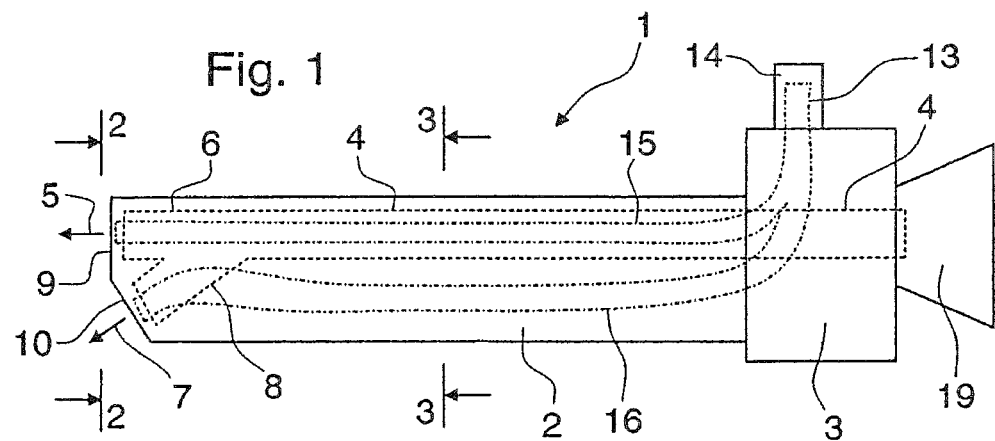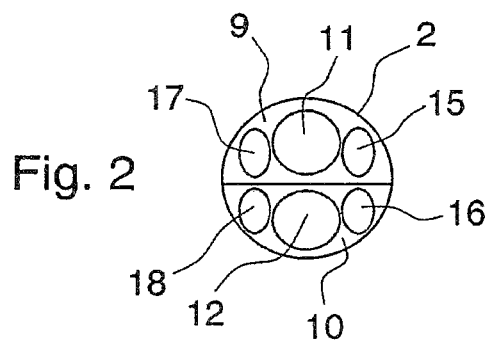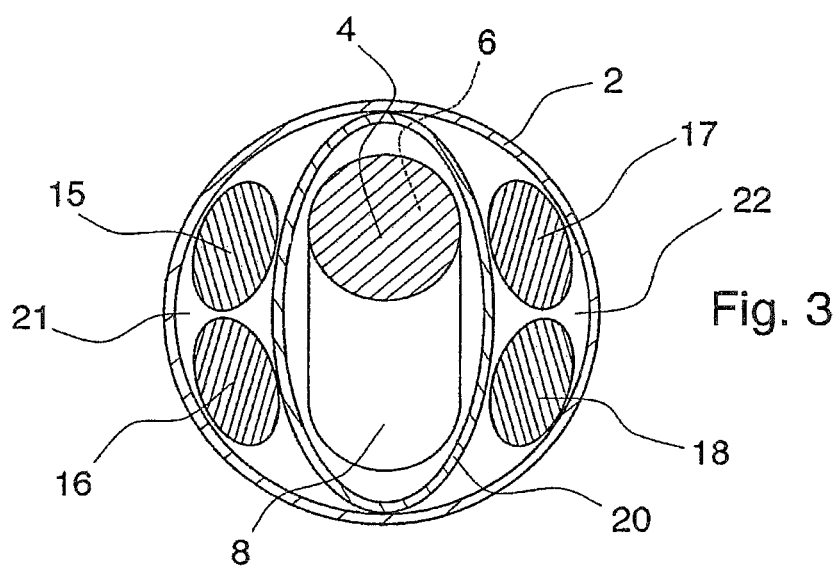

ENDOSCOPE HAVING A SHAFT TUBE

CROSS-REFERENCE TO RELATED APPLICATION

The present application is based upon and claims the benefit of priority from PCT/EP2011/005284 filed on Oct. 20, 2011, which claims benefit to DE 10 2010 056 025.1 filed on Dec. 27, 2010, the entire contents of each of which are incorporated herein by reference.

BACKGROUND

1. Field

The present invention generally relates to endoscopes, and more particularly to an endoscope of the type referred to in claim 1.

2. Prior Art

Endoscopes of this type have an elongated shaft intended for introduction into the body to be examined, which consists essentially of two metal tubes, the outer shaft tube, which forms the stable and sealing outer wall of the shaft, and the fibre tube, which is located on the inside and delimits the free cross-section intended to accommodate the fibres of the optical fibre bundle toward the inside, thus with respect to the image guide.

A design of this class is disclosed in DE 10 2007 002 042 B4. In the usual design, the image guide is round. It consists, for example, of the round lenses of a set of relay lenses or an image guide fibre bundle with a round cross-section. Correspondingly, the fibre tube is also round. The free cross-section between the two tubes has the usual half-moon-shaped cross-section.

The image guide with its distally positioned objective must be accommodated in the round cross-section of the fibre tube, which is unproblematic in the case of the usual rotationally symmetric design of image guides. More and more often, however, endoscopes with two viewing directions are being designed, as is shown for example by DE 10 2009 020 262 A1. In this way, it is possible to look, for example alternately, in the straight-ahead direction and a direction at an angle to this. In this case the image guide can remain round essentially over its length. In the distal end region, thus in the area of the objective, widening of the cross-section in the direction of the objective section is necessary for the oblique viewing direction. This leads to design problems. The invention can also be used in an endoscope with a continuously adjustable viewing direction, as is known from DE 10 2009 049 843 B3.

If one attempts to place this distal cross-sectional widening in a round fibre tube, the latter must be enlarged. This leads to a substantial narrowing of the free cross-section and thus to a decrease in the number of optical fibres. The light transmission deteriorates, and the image becomes darker. In addition, the half-moon-shaped free cross-section between the two tubes presents a number of drawbacks with regard to accommodating the optical fibre bundle. For example, it limits the possibilities for the distal arrangement of the radiating surface of the optical fibre bundle.

SUMMARY

An objective of the present invention consists of reducing the problems relating to the configuration of the fibre tube.

According to the invention, the fibre tube is designed with an elongate cross-section. In this way, the possibility is created of advantageously fitting an objective into the fibre tube, said objective being designed for two viewing directions and being larger in one cross-sectional direction than perpendicular to this.

Thereby, through the oval design of the fibre tube, its cross-sectional area is kept relatively small, so that a large free cross-section remains between the tubes, in which thus a large amount of light can be transported. On the other hand, advantageously, the possibility exists of using the cross-sectional configuration resulting according to the invention to form two partial cross-sections within the shaft tube on either side of the oval fibre tube, in which respective separate parts of the optical fibre bundle can be placed. Compared to the unfavourable cross-sectional shape of the free cross-section in the known design, therefore, the possibility of a more symmetric light emission results.

Advantageously, two partial bundles of the optical fibre bundle are disposed in each of the partial cross-sections, one of which in each case can be made to emit light in the straight-ahead direction and the other at an angle, so that excellent illumination is achieved.

Advantageously, the shaft tube is round. This is a cross-sectional shape that is highly suitable for the design according to the invention, which also has the advantage of good availability. For the same reasons, the fibre tube is advantageously oval.

BRIEF DESCRIPTION OF THE DRAWINGS

In the drawing, the invention will be illustrated by way of example and schematically. The Figures show:

FIG. 1 illustrates a side view of an endoscope according to the invention and FIGS. 2 and 3 illustrate sections taken along lines 2-2 and 3-3, respectively, in FIG. 1.

DETAILED DESCRIPTION

FIG. 1 shows a side view of an endoscope 1 with a shaft surrounded by a shaft tube 2, which extends distally from a main body 3.

In the interior of the shaft tube 2, an image guide 4, shown by broken lines in FIG. 1, is disposed; in its distally located objective area it has an objective part 6 that looks straight ahead in the direction of the arrow 5, and an objective part 8 that looks at an angle in the direction of the arrow 7.

The end face of the shaft of the endoscope 1 consists of two end face parts 9 and 10 at an angle to one another, shown in front view in FIG. 2. Here the end face part 9 is perpendicular to the arrow 5 and the end face part 10 is perpendicular to the arrow 7, thus in each case perpendicular to the viewing direction. In each of the end face parts a window 11 or 12 is disposed, through which the objective part 6 or 8 can look in the direction of the arrow 5 or 7 respectively.

To simplify the graphical representation, the viewing direction 5 is shown looking straight ahead, thus in the direction of the axis of the shaft tube 2, and the viewing direction 7 is at a 45° angle. Instead, more common viewing directions are about 12° for viewing direction 5 and about 30° for viewing direction 7.

For illuminating the field of view that can be observed through the windows 11, 12, an optical fibre bundle 13 is provided, the proximal end of which lies in an optical fibre connecting port 14, which in the usual design emerges from the side of the main body 3 and in a known embodiment can be designed for connecting an optical fibre cable, with which light can be transmitted from a remote light source to the proximal end of the optical fibre bundle 13 and connected into it at that point.

In the main body 3 the optical fibre bundle 13 splits into a total of four partial bundles 15, 16, 17 and 18, which can be seen in the cross-section of FIG. 3. In FIG. 1, only the two partial bundles 15 and 16 located toward the observer can be seen. The partial bundles 17 and 18 run parallel to the partial bundles 15 and 16.

At the distal ends, the partial bundles are parallel to the objective parts 6 and 8 and to the arrows of the viewing directions 9 and 10 and terminate in the end face parts 9 and 10 with their light-emitting end surfaces, as is shown in FIG. 2.

Alternatively, instead of the one optical fibre bundle 13, two such bundles may be used, which are supplied separately and branch out differently in order to be assigned to one viewing direction each. Comparing this with FIG. 3, one of these bundles can branch out into the partial bundles 16 and 18 and provide for illumination in viewing direction 7, while the other bundle supplies the partial bundles 15 and 17 and thus supplies the straight-ahead viewing direction 5. Thus by turning the two bundles off and on, the light can be separately guided in directions 5 and 7.

As FIG. 1 shows, the image guide 4 ends proximally in an eyepiece 19, instead of which a video camera may also be connected. Instead of the image guide 4 travelling lengthwise through the shaft tube 2, in the distal end area at the point at which the objective parts 6 and 8 are combined into a common image guide 4, a video camera may be disposed.

FIG. 3 shows, looking in the distal direction, a cross-section of the shaft tube 2 with cut image guides 4 and the cut partial bundles 15, 16, 17 and 18 of the optical fibre bundle. Here also, a fibre tube 20 is shown in cut view, which over the total length of the shaft tube 2 separates the image guides 4, 6, 8 from the optical fibre bundles, thus the partial bundles 15 to 18. The fibre tube 20 is designed with an oval cross-section, an in particular, with a cross-section constant over the length, to reduce manufacturing problems. In its oval cross-section it can accommodate the two objective parts 6 and 8, which are on top of one another in the representation of FIG. 3, in a relatively unproblematic manner.

The free cross-section remaining between the two tubes 2 and 20 is divided into two partial cross-sections 21 and 22 in the design shown in FIG. 3; in the embodiment shown they are actually completely separate from one another, since the two tubes 2, 20 touch only along two lines.

The partial cross-sections 21 and 22 present advantageous cross-sectional shapes for accommodating the partial bundles 15 and 16 or 17 and 18.

Deviating from the cross-sections shown, other cross-sectional shapes may also be used. For example, the shaft tube 2 could be made with a polygonal cross-section or could likewise be oval, but advantageously with its largest cross-section perpendicular to that of the fibre tube 20. The fibre tube 20 can also be designed with a different cross-section, e.g., elongate rectangular.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscope comprising:
a shaft tube;
a fibre tube disposed in a longitudinal direction within the shaft tube;
an image guide having a distal objective, the image guide being disposed within the fibre tube; and
an optical fibre bundle disposed in a cross-sectional area between the fibre tube and the shaft tube;
wherein the fibre tube has a lumen having an elongate cross-section in a plane perpendicular to the longitudinal direction;
the elongate cross-section is constant over a length of the shaft tube; and
the distal objective comprises first and second distal objectives corresponding to first and second viewing directions, one of the first and second distal objectives extending in a first direction from the other of the first and second distal objectives, the fibre tube being oriented such that a larger dimension of the elongate cross-section corresponds with the first direction to accommodate cross-sectional areas of the first and second distal objectives within the elongate cross-section of the fibre tube.

2. The endoscope according to claim 1, wherein the fibre tube is disposed in the shaft tube such that the fibre tube divides the cross-sectional area into first and second cross-sectional areas, wherein the optical fibre bundle branches into a plurality of bundle portions in a proximal end area and the plurality of bundle portions are disposed in the first and second cross-sectional areas.

3. The endoscope according to claim 2, wherein the plurality of bundle portions comprise four bundle portions, wherein two of the four bundle portions are disposed in each of the first and second cross-sectional areas.

4. The endoscope according to claim 1, wherein the shaft tube is round in cross-section.

5. The endoscope according to claim 1, wherein the fibre tube is oval in cross-section.

* * * * *